United States Patent [19]

Häberle et al.

[11] Patent Number: 5,399,290
[45] Date of Patent: Mar. 21, 1995

[54] LIQUID CRYSTALS WITH (POLYSILA) ALKYL WING GROUPS

[75] Inventors: Norman Häberle, Munich; Franz-Heinrich Kreuzer, Martinsried; Benno Krueger, Unterhaching; Ingo Zahn, Munich, all of Germany

[73] Assignee: Consortium für elektrochemische Industrie GmbH, Munich, Germany

[21] Appl. No.: 984,599

[22] Filed: Dec. 2, 1992

[30] Foreign Application Priority Data

Dec. 6, 1991 [DE] Germany .................. 41 40 352.5

[51] Int. Cl.⁶ .................. C09K 19/52; C07F 7/08; G02F 1/13
[52] U.S. Cl. .................. 252/299.01; 252/299.61; 252/299.63; 252/299.66; 252/299.67; 549/369; 556/462; 556/466; 359/103
[58] Field of Search .................. 252/299.01, 299.61, 252/299.63, 299.66, 299.67, 299.62; 544/298; 546/14; 549/369; 556/462, 466; 359/103

[56] References Cited

U.S. PATENT DOCUMENTS

| | | | |
|---|---|---|---|
| 4,358,391 | 10/1982 | Finkelmann et al. | 252/299.01 |
| 4,410,570 | 2/1982 | Kreuzer et al. | 252/299.01 |
| 5,106,530 | 4/1992 | Haas et al. | 252/299.6 |
| 5,158,702 | 6/1990 | Hass et al. | 252/299.6 |

FOREIGN PATENT DOCUMENTS

| | | |
|---|---|---|
| 0029162 | 11/1980 | European Pat. Off. |
| 0060335 | 10/1981 | European Pat. Off. |
| 0404140 | 6/1990 | European Pat. Off. |
| 0405326 | 2/1991 | European Pat. Off. |
| 3827600 | 8/1988 | Germany |
| 3920509 | 6/1989 | Germany |
| 1144491 | 12/1987 | Japan |

OTHER PUBLICATIONS

H. Finkelmann et al., Makromol. Chem. Rapid Commun. 1, 31–34 (1980) "Synthesis and Characterization of Linear Polymers".

C.A. 111, 205667e (1989), "Ferroelectric chiral smectic liquid crystal materials".

*Primary Examiner*—Shean Wu
*Attorney, Agent, or Firm*—Martin Connaughton

[57] ABSTRACT

A compound of the general formula $$M-(CH_2)_n-(O)_m-[-D-B-]_q-Y, \qquad (I)$$

in which M represents a silicon radical having 2 to 5 silicon atoms which are linked together by bridging elements A, and the remaining valencies of the silicon atoms are saturated with radicals R; A is a bridging element selected from the group consisting of $C_1$- to $C_8$-alkylene radicals and oxygen with the proviso that at least one radical A per M radical is a $C_1$- to $C_8$-alkylene radical; R represents optionally fluorine or chlorine atom- or cyano group-substituted straight-chain $C_1$- to $C_{10}$-alkyl or $C_2$- to $C_{10}$-alkenyl radicals, branched chain $C_3$- to $C_{10}$-alkyl or $C_3$- to $C_{10}$-alkenyl radicals, optionally $C_1$- to $C_4$-alkyl-, $C_1$- to $C_4$-alkoxy radicals, fluorine, chlorine, bromine atom, cyano, trifluoromethyl or nitro radical substituted $C_6$- to $C_{12}$-cycloalkyl, $C_6$- to $C_{12}$-cycloalkenyl, $C_6$- to $C_{12}$-alkylcycloalkyl, $C_6$- to $C_{12}$-alkylcycloalkenyl, $C_6$- to $C_{12}$-aryl or $C_6$- to $C_{12}$-aralkyl radicals; n is an integer of from 3 to 12; m is 0 or 1; D represents isocyclic or heterocyclic saturated or unsaturated 5- or 6-membered rings; B represents a linking group selected from the group consisting of a chemical bond, a —COO—, —OOC—, —CH$_2$—CH$_2$—, —CH=CH—, —C≡C—, —CH=N—, —N=CH—, —CH$_2$—O—, —O—CH$_2$— and —N=N— group; q is an integer of from 1 to 3; Y is a hydrogen atom or a straight-chain or branched chain $C_1$- to $C_{10}$-alkyl or $C_1$- to $C_{10}$-alkoxy group or a radical D which is provided with a hydrogen atom or substituted, in which 1 or 2 ring substituents may be $C_1$- to $C_4$-alkyl, $C_1$- to $C_4$-alkoxy radicals, fluorine, chlorine or bromine atoms, cyano, trifluoromethyl or nitro radicals, or a cholesteryl radical.

These compounds are liquid crystals and can be employed alone or in admixture with other liquid crystals.

8 Claims, No Drawings

LIQUID CRYSTALS WITH (POLYSILA) ALKYL WING GROUPS

The invention relates to novel liquid crystals which contain in the wing groups a plurality of Si atoms which are linked together by alkylene radicals, processes for preparing the same and the use thereof.

BACKGROUND OF THE INVENTION

The use of silicon in liquid crystals is known in principle but it is, in particular, polymeric liquid crystals having poly- or oligosiloxane backbone in linear or cyclic arrangement with different mesogenic side chains which are described, for example, by H. Finkelmann and G. Rehage in Macromol. Chem. Rapid Commun. 1, 31, (1980), or else in EP-A 29 162 (Finkelmann et al.; laid open for public inspection on May 27, 1981, Wacker-Chemie GmbH). Cyclosiloxanes with mesogenic side groups are disclosed in EP-A 60 335 (Kreuzer et al.; laid open for public inspection on Sept. 22, 1982, Consortium für elektrochemische Industrie GmbH).

In addition, monomeric liquid crystals which use in the wing groups either trialkylsilyl radicals, as in DE-A 38 27 600 (Hemmerling et al.; laid open for public inspection on Feb. 15, 1990, Hoechst AG), or polymethyloligosiloxanes, as in JP 89/144491 (laid open for public inspection on Jun. 6, 1989, abstracted in Chemical Abstracts, Vol. 111, 205 667 e (1989), or EP-A 404 140 (Haas et al.; laid open for public inspection on Dec. 27, 1990, Consortium für elektrochemische Industrie GmbH) are also known. Owing to these silanyl or siloxanyl radicals, the resulting properties are changed from those of the unsilylated compounds. This relates in particular to melting point depressions, phase broadening and changes in the types of phases. The trialkylsilyalkylcontaining liquid crystals however result in smaller modifications compared with unsilylated compounds. Although the siloxanylsubstituted derivatives have more of an effect in this sense, their chemical resistance is low and, specifically in the case of larger siloxanes, they can be prepared in pure form only with difficulty because higher siloxanes can often be obtained only in mixtures which are difficult to separate. The lack of chemical stability of the Si—O bonds means that the introduction of the siloxanyl radicals must be the last chemical reactions of the syntheses in order not to decompose the entire molecule again. However, this requirement cannot be met when, as frequently occurs in liquid crystals, hetero atoms such as nitrogen or sulfur are present, which prevent silylation or siloxanation.

Therefore, it is an object of the present invention to provide liquid crystals which are easier to prepare and more chemically resistant and have improved liquid crystalline properties such as wider phase ranges and lower melting points.

SUMMARY OF THE INVENTION

The foregoing object and others which will become apparent from the following description is accomplished in accordance with this invention, generally speaking by providing compounds of the general formula

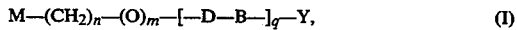

$$M-(CH_2)_n-(O)_m-[-D-B-]_q-Y, \quad (I)$$

in which M represents a radical composed of 2 to 5 silicon atoms in linear, branched or cyclic arrangement, which are linked together by bridging elements A, the remaining valencies of the silicon atoms being saturated with radicals R; A represents $C_1$- to $C_8$-alkylene radicals or oxygen as bridging elements, with the proviso that at least one radical A per M radical represents a $C_1$- to $C_8$-alkylene radical; R represents the same or different, optionally fluorine or chlorine atom- or cyano group-substituted straight-chain $C_1$- to $C_{10}$-alkyl or $C_2$- to $C_{10}$-alkenyl radicals, branched chain $C_3$- to $C_{10}$-alkyl or $C_3$- to $C_{10}$-alkenyl radicals, optionally $C_1$- to $C_4$-alkyl-, $C_1$- to $C_4$-alkoxy radicals, fluorine, chlorine or bromine atoms, cyano, trifluoromethyl or nitro radical substituted $C_6$- to $C_{12}$-cycloalkyl, $C_6$- to $C_{12}$-cycloalkenyl, $C_6$- to $C_{12}$-alkylcycloalkyl, $C_6$- to $C_{12}$-alkylcycloalkenyl, $C_6$- to $C_{12}$-aryl or $C_6$- to $C_{12}$-aralkyl radicals; n represents an integer of from 3 to 12; m represents 0 or 1; D represents the same or different isocyclic or heterocyclic saturated or unsaturated 5- or 6-membered rings; B represents the same or different linking groups selected from a chemical bond, a —COO—, —OOC—, —$CH_2$—$CH_2$—, —CH=CH—, —C≡C—, —CH=N—, —N=CH—, —$CH_2$—O—, —O—$CH_2$— and —N=N— group; q represents an integer of from 1 to 3; Y represents a hydrogen atom or a straight-chain or branched chain $C_1$- to $C_{10}$-alkyl or $C_1$- to $C_{10}$-alkoxy group or a radical D which is provided with a hydrogen atom or substituted, in which 1 or 2 ring substituents may be $C_1$- to $C_4$-alkyl, $C_1$- to $C_4$-alkoxy radicals, fluorine, chlorine or bromine atoms, cyano, trifluoromethyl or nitro radicals, or represents a cholesteryl radical.

Where it is possible from the individual structures of the radicals R, the invention also relates to optical isomers both in pure form and in the form of their mixtures, for example of the corresponding racemates.

DESCRIPTION OF THE INVENTION

The wing groups M of the liquid crystals of this invention of the general formula I have silane radicals. These wing groups are linked via the spacer group $(CH_2)_n$—$(O)_m$ to a widely variable mesogenic group $[-D-B-]_q$.

Smaller values than 3 for n give a spacer group which is too short and together with an oxygen atom when m has the value of 1, results in a spacer group which is labile to chemical and thermal effects.

Preferred bridging elements A are straight-chain alkylene radicals such as the methylene, 1,2-ethylene, 1,3-propylene, 1,4-butylene, 1,5-pentylene, 1,6-hexylene, 1,7-heptylene or 1,8-octylene group.

Preferred radicals D are 1,4-phenylene radicals, 1,4-cyclohexylidene radicals, 1,4-cyclohexenylidene radicals, 2,5- or 3,6-pyridinediyl radicals, 2,5-pyrimidinediyl radicals, 2,5-pyridazinediyl radicals, 2,5-triazinediyl radicals, 2,5-dioxanediyl radicals, 2,5-tetrahydrofurandiyl radicals, 1,3,4-thiadiazole-2,5-diyl radicals or 1,4-bicyclo[2.2.2]octanediyl radicals.

Examples of radicals R are alkyl radicals such as the methyl, ethyl, n-propyl, iso-propyl, n-butyl, iso-butyl, tert-butyl, n-pentyl, iso-pentyl, neo-pentyl, tert-pentyl radical; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; alkenyl radicals such as the vinyl and the allyl radical; cycloalkyl radicals such as cyclopentyl, cyclohexyl, cycloheptyl radicals and methylcyclohexyl radicals;

cycloalkenyl radicals such as the cyclohexenyl radical; aryl radicals such as the phenyl and the napthyl radical; aralkyl radicals such as o-, m-, p-tolyl radicals; xylyl radicals; ethylphenyl radicals; benzyl radicals; the alpha- and the β-phenylethyl radical.

The above examples of alkyl radicals also relate to the alkyl radicals in the alkoxy groups.

The examples of the alkyl and alkoxy radicals also relate to Y.

Preferred liquid-crystalline compounds of formula I are compounds in which M represents a radical composed of 2 to 5 silicon atoms in linear or branched arrangement, which are linked together by bridging members A, the remaining valencies of the silicon atoms being saturated with radicals R; A represents a methylene, 1,2-ethylene or 1,3-propylene group or an oxygen atom with the proviso that at least one radical A per radical M represents a methylene, 1,2-ethylene or a 1,3-propylene group,; R represents the same or different $C_1$- to $C_4$-alkyl radicals, where one of the radicals located on the terminal silicon atom is selected from straight-chain $C_1$- to $C_{10}$-alkyl or alkenyl radicals, fluorine or chlorine atom-substituted $C_1$- to $C_5$-alkyl radicals, branched $C_3$- to $C_{10}$-alkyl or $C_3$- to $C_{10}$-alkenyl radicals, optionally $C_1$- to $C_4$-alkyl, $C_1$- to $C_4$-alkoxy radicals, fluorine, chlorine or bromine atoms, cyano, trifluoromethyl or nitro radical substituted $C_6$- to $C_{12}$-cycloalkyl, $C_6$- to $C_{12}$-cycloalkenyl, $C_6$- to $C_{12}$-alkylcycloalkyl, $C_6$- to $C_{12}$-alkylcycloalkenyl, $C_6$- to $C_{12}$-aryl or $C_6$- to $C_{12}$-aralkyl radicals; n represents an integer of from 3 to 10; m represents the value 0 or 1, D represents the same or different radicals selected from 1,4-phenylene radicals, 1,4-cyclohexylidene radicals, 2,5-or 3,6-pyrimidinediyl radicals, 2,5-dioxanediyl radicals, or 1,4-bicyclo[2.2.2]octanediyl radicals; B represents the same or different linking groups selected from a chemical bond, a —COO—, —OOC—, —CH$_2$—CH$_2$— or a —CH=CH— group; q represents an integer of from 1 to 3; Y represents a hydrogen atom or a straight-chain or branched chain $C_1$- to $C_{10}$-alkyl or $C_1$- to $C_{10}$alkoxy group or a phenyl radical which is provided with a hydrogen atom or substituted, or cyclohexyl or cyclohexenyl radical which is provided with a hydrogen atom or substituted, it being possible, where appropriate, for 1 or 2 substituents which occur to be $C_1$- to $C_4$-alkyl, $C_1$- to $C_4$-alkoxy radicals, fluorine or chlorine atoms or cyano radicals, or represents a cholesteryl radical.

In the especially preferred compounds of the general formula I, n represents an integer of from 4 to 8; m represents the value 0 or 1; D represents the same or different radicals selected from 1,4-phenylene or 1,4-cyclohexylidene radicals; B represents the same or different linking groups selected from a chemical bond, a —COO—, —OOC—, or a —CH$_2$—CH$_2$— group; q represents the value 1 or 2; Y represents a hydrogen atom or a straight-chain or branched chain $C_1$- to $C_{10}$-alkyl or $C_1$- to $C_{10}$-alkoxy group or a phenyl or cyclohexyl radical which is provided with a hydrogen atom or substituted, it being possible, where appropriate, for 1 or 2 substituents which occur to be $C_1$- to $C_4$-alkyl, $C_1$- to $C_4$-alkoxy radicals, fluorine or chlorine atoms or cyano radicals, or represents a cholesteryl radical; M represents a radical of the general formula:

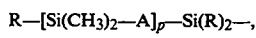

R—[Si(CH$_3$)$_2$—A]$_p$—Si(R)$_2$—,  (II)

in which A represents a methylene group; R represents a straight-chain $C_1$- to $C_4$-alkyl group or a phenyl radical and p represents the value 1 or 2.

All the radicals R in the general formula II are preferably methyl groups. The compounds of this invention are prepared according to this invention in a manner known per se by the following processes:

Process A:

The compounds of the above general formula I can be prepared by reacting compounds of the general formula MH with compounds of the general formula

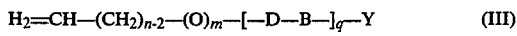

H$_2$=CH—(CH$_2$)$_{n-2}$—(O)$_m$—[—D—B—]$_q$—Y   (III)

in the presence of at least one metal of the platinum group and/or of its compounds, where M, A, R, n, m, D, B, q, Y and p are the same as above with the proviso that the hydrogen atom in MH is bonded to a silicon atom.

The required silanes of the general formula MH in which M, R, A and p have the same meaning as in general formula I, can be obtained by known processes such as, for example, Grignard syntheses from alkylsilylmethylmagnesium halides with alkylsilyl halogen compounds or from hydrosilyation reactions of alkyl—Si—H derivatives with alkenylalkylsilane derivatives with Pt catalysis or by pyrolysis of alkylsilanes. Branched silanes can also be obtained in the same manner but can also be prepared by pyrolysis of alkylsilanes. Oligosilacycloalkanes are also obtainable by the latter process. An example which may be mentioned is the preparation of 1,1,3,3,5-pentamethyl-1,3,5-trisilacyclohexane (G. Fritz et al., Z. anorg. all. Chem, 1980, 460, pp. 115-143).

The preparation of compounds having terminal double bonds, which can thus be hydrosilylated, of the general formula III in which n, m, D, B, q and Y are the same as in general formula I is likewise known.

For example, the alkenyl radical can be introduced by reacting the corresponding alkenyl halides with corresponding organometallic benzene derivatives, in particular the Grignard compounds or organolithium compounds. Preferred examples of such benzene derivatives are 4-halogenophenylmagnesium halides. The alkenyl halide is reacted with the benzene derivative preferably in an inert solvent (mixture), for example diethyl ether, methyl tert-butyl ether, tetrahydrofuran, 1,4-dioxane, hydrocarbons and their mixtures such as benzene, toluene, xylenes, mixtures of hexane isomers or petroleum ether. The reaction is preferably carried out at temperatures from −100° C. to +100° C., in particular under pressures from 0.09 to 0.11 MPa (abs.). The reaction can in some cases be speeded up by ultrasound.

4(ω- Alkenyl)-1-halogenobenzenes prepared in this manner can be reacted in known manner per se, inter alia a second time with magnesium to give the corresponding organomagnesium halides and subsequently with CO$_2$ to give 4-(ω-alkenyl)benzoic acids and finally to give the corresponding, optionally substituted phenyl esters.

4- (ω-Alkenyl)phenol derivatives can be obtained by reacting 4-ω-alkenylmagnesium halides with 4-halogenophenols protected on the hydroxyl group, where appropriate with catalysis such as dilithium tetrachlorocuprate. The phenols which can be obtained in this manner can be esterified with appropriate acids or acid derivatives. Reference is made to DE-A 39 35 638 and DE-A 40 22 151 for the preparation of 4-(ω-alkenyl)phenyl derivatives.

4-(ω-Alkenyl)benzaldehydes can be obtained by reacting 4-(ω-alkenyl)phenylmagnesium halides (which can be prepared as described above) with N,N-dimethylformamide and in turn reacted with primary amines, for example, with the commercially available 4-alkylanilines to give the corresponding azomethines (Schiff's bases).

Reaction of the 4-(ω-alkenyl)benzaldehydes which can be prepared by the above process with suitable derivatives, for example alkanephosphonic esters (Wittig-Horner reaction) results in 4-(ω-alkenyl)phenylethylenediyl derivatives.

According to EP-A 168 683, Example 26, 1-(ω-alkenyl)-4nitrobenzene can be reduced to 4,4'-di(ω-alkenyl)azoxybenzene, for example using magnesium turnings in methanol as solvent. The latter can in turn be reduced in a known manner to the corresponding azobenzene, for example by zinc and sodium hydroxide solution.

Heterocyclic elements D can likewise be obtained in a known manner. Thus, instead of aromatic rings it is also possible for substituted heterocyclics, some of which can also be purchased, to be employed or else to be prepared by ring synthesis. Thus, for example, the dioxanes can be obtained by reacting 2-(M-alkyl)1,3-diols with 4-substituted benzaldehyde derivatives. The 2-(M-alkyl)1,3-diols required for this can be obtained by reducing 2-(M-alkyl)malonic diesters with lithium aluminum hydride, and these diesters by hydrosilylation of 2-ω-alkenyl)malonic diesters, some of which are available commercially. Examples of this reaction sequence are shown in the Examples.

The pyrimidine derivatives can be obtained in a manner known per se, for example by converting 4-(M-alkyloxy)benzonitriles via 4-(M-alkyloxy)benzimidoyl chlorides into 4-(M-alkyloxy)benzamidines. These benzamidine derivatives can be cyclized, likewise in a known manner, with substituted malonaldehyde bis(-dialkyl)acetals to form the desired pyrimidine derivatives.

The catalyzed hydrosilylation of the terminal double bonds is likewise a known and widely used method. Examples of catalytically active metals of the platinum group and/or their compounds, hereinafter referred to as platinum catalyst, which are able to speed up the process of this invention are platinum, palladium, rhodium, iridium and their compounds, preferably platinum and/or its compounds. It is possible to employ for this purpose all catalysts which have also been employed to date for the addition of hydrogen atoms directly bonded to Si atoms onto unsaturated aliphatic compounds. Examples of such catalysts are metallic and finely divided platinum, which can be present on supports such as silicon dioxide, aluminum oxide or active carbon, compounds or complexes of platinum such as platinum halides, for example $PtCl_4$, $H_2PtCl_6 \cdot 6H_2O$, $Na_2PtCl_4 \cdot 4H_2O$, platinum-olefin complexes, platinum-alcohol complexes, platinum-alcoholate complexes, platinum-ether complexes, platinum-aldehyde complexes, platinum-ketone complexes, including products of the reaction of $H_2PtCl_6 \cdot 6H_2O$ and cyclohexanone, platinum-vinylsiloxane complexes with or without a detectable amount of inorganically bonded halogen, bis(gammapicoline) platinum dichloride, trimethylenedipyridine platinum dichloride, dicyclopentadienyl-platinum dichloride, dimethyl sulfoxide ethyleneplatinum(II) dichloride and products of the reaction of platinum tetrachloride with olefin and primary amine or secondary amine or primary and secondary amine, such as the product of the reaction of platinum tetrachloride dissolved in 1-octene with sec-butylamine, or ammoniumplatinum complexes according to EP 110 370.

The platinum catalyst is preferably used in amounts of from 0.02 to 50 mol percent, calculated as elemental platinum and based on the number of mols of the reaction component which is present in less than the stoichiometric amount or in the stoichiometric amount.

The reaction is preferably carried out at temperatures of from 0° C. to 150° C., and more preferably from 10° C. to 100° C., preferably under pressures of 0.05 MPa to 2.0 MPa.

If the silane MH or the compound of the general formula III is very unreactive, it is also possible to use higher temperatures, higher pressures and the presence of more platinum catalysts.

The reaction is preferably carried out in an inert solvent which should, in particular, be aprotic; solvents or solvent mixtures with a boiling point or boiling range of up to 160° C., and more preferably up to 120° C., under 0.1 MPa (abs.).

Examples of suitable solvents are esters such as methyl acetate, ethyl acetate, n- and iso-propyl acetate, n-, sec- and t-butyl acetate, ethyl formite and diethyl carbonate; ethers such as dioxane, tetrahydrofuran, diethyl ether, di-n-propyl ether, diisopropyl ether, di-n-butyl ether, ethylene glycol dimethyl ether, ethylene glycol monoethyl ether, diethylene glycol dimethyl ether and anisole; chlorinated hydrocarbons such as dichloromethane, trichloromethane, tetrachloromethane, 1,2-dichloroethane, trichloroethylene, tetrachloroethylene and chlorobenzene; hydrocarbons such as pentane, n-hexane, mixtures of hexane isomers, cyclohexane, heptane, octane, cleaner's naphtha, petroleum ether, benzene, toluene, xylenes; ketones such as acetone, methyl ethyl ketone, methyl isobutyl ketone or mixtures of these solvents.

The term solvent does not mean that all the components in the reaction must be soluble therein. The reaction can also be carried out in a suspension or emulsion of one or more reactants. The reaction can also be carried out in a mixture of solvents with a miscibility gap, in which at least one reactant is soluble in each of the mixed phases.

The silyl component MH is preferably employed in the process of this invention in a molar ratio of 1:2 to 2:1, and more preferably from 1:1.1 to 1.1:1, with the compound to be added on according to the above reaction equation.

Further details on the known preparation processes are to be found in Houben-Weyl, Methoden der organischen Chemie (Methods of Organic Chemistry), Georg Thieme Verlag, Stuttgart and New York. Other possibilities are described in the examples.

Process B:

The compounds of the general formula I can be prepared by reacting halogenosilane compounds of the general formula M—Hal in which Hal represents a chlorine, bromine or iodine atom with organometallic compounds of the general formula

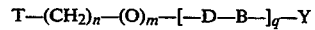

$$T-(CH_2)_n-(O)_m-[-D-B-]_q-Y \qquad (IV)$$

in which T represents an alkali metal atom or Mg—Hal, where Hal is the same as above, with the elimination of a metal halide T—Hal. In Process B, M, A, R, n, m, D, B, q, Y and p are the same as in general formulas I and II with the proviso that in the case where B and/or Y react with alkali metals or magnesium or compounds of the general formula IV, B and/or Y are introduced only after the reaction of M—Hal with compounds of the general formula IV has occurred.

Examples of groups B and Y which react with alkali metals or magnesium or compounds of the general formula IV are carboxyl derivatives and cyano groups.

The reaction rate in Process B can be increased by catalysts such as iron(III) chloride or dilithium tetrachlorocuprate and/or dilithium tetrabromocuprate or dichloro(bisdiphenylphosphinopropane)nickel. In regard to the sequence of the reaction steps which lead to various elements, D, B, q and y, the same applies in Process B as in Process A.

Process C:

The compounds of the general formula I can be prepared by reacting compounds of the general formula

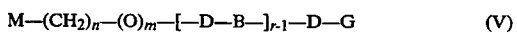

$$M-(CH_2)_n-(O)_m-[-D-B-]_{r-1}-D-G \qquad (V)$$

with compounds of the general formula

$$Q-[-D-B-]_s-Y \qquad (VI)$$

where r and s each are integers of from 0 to 3 whose total is q, G and Q each have the meaning of one of the radicals —OH, —OLi, —ONa, —OK, —O—$C_1$- to —O—$C_4$—alkyl, —COOH, —COBr, —COCl, —$NH_2$, —O—tos or —MgHal and M, A, R, n, m, D, B, q, Y and p are the same as in formulas I and II and Hal represents the chlorine, bromine or iodine atom. Process C entails B groups being formed with elimination of compounds W meaning water, $C_1$- to $C_4$-alkanol, HHal, $MgHal_2$, LiHal, NaHal, KHal, Li—O—tos, Na—O—tos or K—O—tos, in which the 4-methylphenylsulfonyl group is referred to as tos.

The starting materials required for preparing the compounds of the general formulas V and VI can be obtained by the procedures described in Process A.

Other Processes:

Another possibility for preparing the compounds of the general formula I is to react compounds of the general formula

$$M-(CH_2)_n-Z \qquad (VII)$$

with compounds of the general formula

$$N-O-[-D-B-]_q-Y \qquad (VIII)$$

where Z represents a chlorine, bromine or iodine atom or the group O—tos. N represents a hydrogen or sodium atom. Hydrogen chloride, bromide or iodide or Na—O—tos are eliminated in the reaction.

The liquid crystals of this invention or which can be prepared according to this invention with (polysila)alkyl wing groups can be used, for example, in display devices, especially in display devices which are produced using smectic liquid crystals or mixtures thereof. In this case it is possible to use both the pure compounds of this invention and their mixtures with one another and, in particular, also mixtures with liquid crystal compounds with another type of structure. The compounds of this invention are suitable for the preparation of nematic, cholesteric and smectic mixtures, especially for mixtures which are able to form a smectic C phase. However, they can also be used as additives to nematic, smectic or cholesteric phases. The liquid crystals of this invention having (polysila)alkyl wing groups can be used both to prepare liquid crystalline basic mixtures and to alter in a beneficial manner the properties of basic mixtures which have already been prepared, such as, for example, the optical anisotropy, the electrical anisotropy, the spontaneous polarization, the viscosity, the tilt angle, the pitch and the phase behavior.

Owing to the (polysila)alkyl wing groups, the liquid crystals of this invention have considerably more beneficial properties than liquid crystals with siloxanylalkyl wing groups according to DE-A 30 20 509. Even when the molecular form is otherwise completely identical, the liquid crystal phases with the compounds of this invention are broader and have lower melting points and clearing points than liquid crystals containing siloxanylalkyl wing groups and, because of the silicon-carbon bonds, are considerably more stable to chemical reactions.

Despite the known sensitivity of liquid crystalline properties to changes in the molecular form on the one hand and to large substituents in the wing group portion on the other hand, wide ranges of variation in the form of the wing groups are found. Despite the wide variety of types of substituents on the Si atoms of the wing groups, the smectic C phases are substantially retained, whereas the ω-alkenyl wing group compounds used as starting compounds, for example, often have only nematic phases or are crystalline monotropic compounds. The wide range of variation in the wing group portion of the compounds of this invention also allows the modules to be adapted to other required properties of the liquid crystals to be prepared and, on the other hand, allows the remaining portions of the molecules (mesogenic portions) to be chosen freely over a wide range.

The content of the liquid crystals of this invention with (polysila)alkyl wing groups in liquid crystal mixtures can vary within wide limits depending on the purpose of use. It can be, for example, from 1% by weight up to 100% by weight.

In the following tables and examples, unless otherwise specified:
(a) all amounts are by weight;
(b) all pressures are 0.10 MPa (abs.); (c) all temperatures are 20° C.

The phase descriptions are given in the following abbreviated manner:
(d) the numbers denote transition temperatures measured in °C.;
(e) the phase types are characterized as follows:
  I: isotropic phase,
  N: nematic phase,
  N*: cholesteric phase,
  $S_A$: smectic A phase,
  $S_C$: smectic C phase, and so on for other smectic phases according to the subscript letter
  $S_C$*: chiral smectic C phase,
  S: smectic state of indeterminate type,
  C: crystalline,
  G: glassy state.
(f) Phase descriptions in parentheses indicate phases which can be supercooled.

EXAMPLE 1

(a) Preparation of 4-(ω-alkenyl)-1-chlorobenzene derivatives

A solution containing 294 g (2 mol) of 1,4-dichlorobenzene in 500 ml of anhydrous tetrahydrofuran was added dropwise under nitrogen at 80° C. to a stirred suspension of 48.6 g (2.0 mol) of magnesium turnings over the course of 110 min. The mixture was then heated at 80°–84° C. for 2 hours, and the solution of the Grignard compound was decanted off the excess magnesium and added dropwise at 80° C. over the course of 30 min to a stirred solution containing 194 g (1.8 mol) of 6-bromo-1-hexene (available from Fluka GmbH, D-7910 Neu-Ulm) in 200 ml of tetrahydrofuran. The mixture was then stirred at 80° C. for 4 hours and poured onto ice. Acidification with hydrochloric acid was followed by extraction three times with a 1:1 diethyl ether/methyl tert-butyl ether mixture, and the ether fractions were stirred with active carbon and dried over sodium sulfate. The residue after concentration of the filtrate was fractionated under reduced pressure. About 156 g (corresponding to a yield of 40% of theory) of 4-(5-hexenyl)-1-chlorobenzene were obtained at a temperature of 116°–118° C. under a pressure of 13 hPa.

The following were prepared analogously:
4-allyl-1-chlorobenzene; (boiling point 66° C. under 13 hPa)
4-(3-butenyl)-1-chlorobenzene; (boiling point 87°–89° C. under 13 hPa)
4-(4-pentenyl)-1-chlorobenzene; (boiling point 102°–105° C. under 13 hPa )
4-(8-nonenyl)-1-chlorobenzene; (boiling point 87° C. under 0.3 hPa)
4-(11-dodecenyl)-1-chlorobenzene; (boiling point 147°–150° C. under 0.2 hPa)

(b) Preparation of 4-(ω-alkenyl)benzoic acids

A Grignard solution was prepared in a known manner from 129 g (0.77 mol) of 4-(3-butenyl)-1-chlorobenzene and 30 g (1.23 mol) of magnesium at 70° C. and cooled. The excess magnesium was removed, and the resultant solution was added dropwise at 15°–25° C. to 300 ml of $CO_2$-saturated tetrahydrofuran, while continuing to pass in $CO_2$. After the addition was complete, the mixture was stirred at room temperature for 1.5 hours and then poured onto 200 g of ice. This was followed by acidification, addition of 300 ml of diethyl ether, extraction by shaking and separation of the phases. The ether phase was washed with water (2 times) and then dried and concentrated. The residue was recrystallized from 600 ml of hexane. About 102.2 g of 4-(3-butenyl)benzoic acid, corresponding to a yield of 77.4% of theory, were obtained. The substance showed the following phase behaviour: C 117N 130 I.

The following were prepared analogously:
4-allylbenzoic acid C 98N 122 I
4-(4-pentenyl)benzoic acid C 76N 96 I
4-(5-hexenyl)benzoic acid C 84N 117 I
4-(9-decenyl)benzoic acid C 80 $S_c$ 85N 108 I
4-(11-dodecenyl)benzoic acid C 83 $S_c$ 107 I The corresponding carbonyl chlorides were prepared from these carboxylic acids in a manner known per se by reaction with thionyl chloride.

4-allylbenzoyl chloride boiling point 115°–116° C. under 8.5 hPa
4-(3-butenyl)benzoyl chloride boiling point 130°–132° C. under 13 hPa
4-(4-pentenyl)benzoyl chloride boiling point 101° C. under 1.5 hPa
4-(5-hexenyl)benzoyl chloride boiling point 95° C. under 0.1 hPa
4-(9-decenyl)benzoyl chloride boiling point 160°–162° C. under 0.04 hPa (c) Preparation of substituted phenyl 4-(ω-alkenyl) benzoate derivatives The esterification is carried out in a known manner by reacting one of the acid chlorides according to (b) with a suitable phenol derivative, stripping off the hydrogen chloride which is formed, or using an auxiliary base such as pyridine or triethylamine in an inert solvent such as toluene or xylene. The phenol derivatives required can in some cases be purchased or can be prepared in a manner known per se.

Preparation of 4-(4-propyl-1-cyclohex-1-enyl)phenyl

4-Bromophenol, which can be purchased, was converted by the method of L. Santucci and H. Gilman, J. Am. Chem. Soc. 1958, 80, p. 4537 with dihydropyran, which can be purchased, to the tetrahydropyranyl ether (THP ether) of 4-bromophenol (yield 90% of theory, boiling point 105° C. under 0.2 hPa). About 2 ml of this THP ether were added under protective gas to 7.3 g of magnesium turnings which had been moistened with tetrahydrofuran, and heated to 50° C. until the Grignard reaction had started. Then the remainder of a total of 64.3 g (0.25 mol) of the THP ether dissolved in THF was added dropwise over the course of 2 hours while stirring at 50°–60° C. After cooling, the solution was decanted off the excess magnesium and added dropwise at 10° C. over the course of 2.5 hours to a solution containing 34.8 g (0.25 mol) of 4-propylcyclohexanone (available from EMS, CH-5605 Dottikon) in 300 ml of toluene. Continuation of the reaction at 80° C. for one hour was followed by cooling, pouring onto ice, acidification and working up of the resulting phases separately. The crude product was cleaved with methanol/hydrochloric acid at 65° C. for 1 hour and then concentrated, dissolved in xylene, mixed with 1 g of p-toluenesulfonic acid and heated under reflux with a water trap for one hour. The mixture was then concentrated, and the residue was fractionated under high vacuum. One fraction which distilled at 160°–190° C. under 0.025 hPa was subsequently recrystallized from cyclohexane. About 11 g (20.4% of theory) of the desired product which melts at 82° C. were obtained.

In the same manner 4- (4-propyl-1-cyclohex-1-enyl)-phenylphenol ($C_{28}H_{32}O_2$; MW 400.6) having a melting point of 221° C. was prepared in a yield of 23.3% of theory from the THP ether of 4-bromo-4'-hydroxybiphenyl.

Preparation of 4-[(4-chlorophenyl)ethyl]phenol

A Grignard solution was prepared as described above from 25.7 g (0.1 mol) of the above mentioned 4-bromophenyl THP ether and added dropwise at 70° C. to a mixture containing 31.1 g of (4-chlorophenyl)ethyl toluenesulfonate (which can be prepared from (4-chlorophenyl)ethanol (available from Aldrich -D-7924;:4: Steinhelm) with known tosylation; melting point 80° C.), a catalytic amount of dilithium tetrachlorocuprate and 50 ml of toluene. The mixture was subsequently heated at 90° C. for 2 hours and then cooled. A voluminous precipitate of lithium tosylate was produced during the course of the reaction. The complete mixture was poured onto ice, acidified and diluted with water until two clear phases which could be separated were produced. Phase separation and working up of the organic phase were followed by liberation of the phenol derivative with methanol/hydrochloric acid, neutralization and concentration. Fractionation of the residue resulted in 76 g of crude product at 155°–170° C. under 0.07 hPa. After the crude product was recrystallized from toluene/petroleum ether, it had a melting point of 108°–109° C.

The following ω-unsaturated esters were prepared by the esterification described,

[4-(4-propyl-1-cyclohex-1-enyl)biphenylyl]4-(9-decenyl)-benzoate; $C_{38}H_{46}O_2$—Phase behaviour: $S_H$ 73 $S_G$ 144 $S_B$ 174 $S_c$ 214 $S_A$ 236N 279 I;

[4-cyanobiphenylyl]4-[4-(3-butenyl)phenylethyl]benzoate;—Phase behavior: C 123N 293 I; $C_{32}H_{27}NO_2$

[4-[2-(4-methoxyphenyl)ethyl]phenyl]-4-(4-pentenyl)-benzoate;—Phase behavior: C 74N 118 I; $C_{27}H_{28}O_3$

[4-(4-propyl-1-cyclohex-1-enyl)phenyl]4-(3-butenyl)-benzoate;—Phase behavior: C 81N 18 1 I; $C_{26}H_{30}O_2$

[4-(4-propyl-1-cyclohex-1-enyl)biphenylyl]-4-(8-nonenyloxy)benzoate;—Phase behavior: $S_H$ 107 $S_G$ 114 $S_I$ 135 $S_c$ 208N 299 I; $C_{37}H_{44}O_3$

[4-(4-nonylcyclohexyl)phenyl]-4-(3-butenyl)benzoate—Phase behavior: C 78 $S_B$ 112N 168 I; $C_{32}H_{44}O_2$ (d) Preparation of 4-(ω-oligoalkyl/arylsilyl)alkylbenzoic ester derivatives by process (a)

About 2.6 g (0.007 mol) of the [4-(4-propyl-1-cyclohex-1-enyl)phenyl]-4- (3-butenyl) benzoate prepared as in (c) above were dissolved in 4.5 ml of methylene chloride, and 1 g (0.007 mol) of 2,2,4-trimethyl-2,4-disilapentane and 0.2 ml of a 0.5% solution of dicyclopentadienylplatinum dichloride (corresponding to 100 ppm Pt) were added, and the mixture was stirred at room temperature. Stirring overnight was followed by concentration and chromatography of the residue on a silica gel column with petroleum ether/ethyl acetate in the ratio 9:1. Fractionation resulted in 2.2 g (60.4% of theory) of a highly pure product which has the following phase behavior: C 45 $S_c$ 86 I. $C_{32}H_{48}O_2Si_2$ (520.7) $(CH_3)_3Si$—$CH_2$—$Si(CH_3)_2$—$(CH_2)_4$—$C_6H_4$—COO—$C_6H_4$—$C_6H_8$-$(CH_2)_2$—$CH_3$.

The following were prepared in an analogous manner:

[4-(4-methoxyphenylethyl)phenyl]-4-(6,6,8,8-tetramethyl-6,8-disilanonyl)benzoate, $C_{33}H_{46}O_3Si_2$, C (N 54) 60 I.

[4-octyloxyphenyl]-4-[4-(5,5,8,8,10,10-hexamethyl-5,8,10-trisilaundecyl)phenylethyl]benzoate, $C_{43}H_{68}O_3Si_3$, $S_I$ 38 $S_c$ 72 I.

[4-(4-propyl-1-cyclohex-1-enyl)]-4-biphenylyl-4-(11,11,14,14,16,16,-hexamethyl-11,14,16-trisilaheptadecyl)benzoate, $C_{48}H_{74}O_2Si_3$, $S_G$ 37 $S_F$ 152 $S_c$ 214 I.

Cholesteryl-4-[4-(5,5,8,8,10,10-hexamethyl-5,8,10-trisilaundecyl)phenylethyl]benzoate, $C_{56}H_{93}O_2Si_3$, C 103 $S_A$ (76 $S_c$) 179 I.

[4-(4-Propyl-1-cyclohex-1-enyl)phenyl]-4-(5 5,8,8-tetramethyl-5,8-disilanonyl)benzoate, $C_{33}H_{50}O_2Si_2$, C 73 $S_E$ 77 $S_c$ 84 I.

Cholesteryl-4-[4-(5,5,8,8,11,11-hexamethyl-5,8,11-trisiladodecyl)phenylethyl]benzoate, $C_{57}H_{95}O_2Si_3$, C 90 $S_A$ (86 $S_c$) 182 I.

[4-(4-Butylphenyl)cyclohexyl]-4-(7,7,9,9-tetramethyl-7,9-disiladecyl)benzoate, $C_{35}H_{56}O_2Si_2$, -11 C 20 $S_B$ 53 I

[4-(4-Propyl-1-cyclohex-1-enyl)phenyl]-4-(5,5,7,7,9,9-hexamethyl-5,7,9-trisiladecyl)benzoate, $C_{35}H_{56}O_2Si_3$, $S_G$ 43 $S_c$ 71 I.

[4-(4-Butylcyclohexyl)phenyl]-4-(7,7,9,9-tetramethyl-7,9-disiladecyl)benzoate, $C_{35}H_{56}O_3Si_2$, C 49 $S_c$ 54N 58 I.

[4-(4-Chlorophenylethyl)-biphenylyl]-4-(10,10,12,12-tetramethyl-10,12-disilatetradecyloxy-1)benzoate, $C_{42}H_{55}ClO_3SI_2$. $S_E$ 172 $S_B$ 217 $S_A$ 251 I.

[4-(4-Propyl-1-cyclohex-1-enyl)phenyl]-4-[10-(4-methyl-cyclohex-3-enyl)-5,5,8,8-tetramethyl-5,8-disilaundecyl]benzoate, $C_{42}H_{63}O_2Si_2$, C ($S_c$ 40) 47 I.

[4- (4-Propyl-1-cyclohex-1-enyl)phenyl]-4-(5,5,7,7,10,10-hexamethyl-6-oxa-5,7,10-trisilaundecyl1)benzoate, $C_{35}H_{56}O_3Si_3$, C 28 $S_c$ 72 I.

[4-Octyloxyphenyl]-4-[4-(5,5,7,7-tetramethyl-5,7-disilaoctyl-phenylethyl]benzoate, $C_{39}H_{58}O_3Si_2$, C ($S_G$44$S_c$) 51 $S_c$ 84 I.

[4-Octyloxyphenyl]-4-[4-(5,5,7-trimethyl-7-phenyl-5,7-disilaoctyl)phenylethyl]benzoate, $C_{44}H_{60}O_3Si_2$, $S_I$ 29 $S_c$ 53 I.

[4-Octyloxyphenyl]-4-[4-(5,5,9,9-tetramethyl-5,9-disiladecyl)phenylethyl]benzoate, $C_{41}H_{62}O_3Si_2$, $S_G$ 44 $S_c$ 83 I.

[4-(4-Propyl-1-cyclohex-1enyl)phenyl]-4-(5,5,8,10,10-pentamethyl-8-trimethylsilylmethyl-5,8,10-trisilaundecyl)benzoate, $C_{39}H_{66}O_2Si_4$, $S_G$ 45 $S_c$ 55 I.

[4-(4-Chlorophenyl)ethylphenyl]-4-(5,5,7,7-tetramethyl-5,7-disilaoctyl)benzoate, $C_{31}H_{41}ClO_2Si_2$, C ($S_E$ 77 $S_B$) 80 $S_B$ 121 I.

[4-(4-Nonylcyclohexyl)phenyl]-4-(5,5,7,7-tetramethyl-5,7-disilaoctyl)benzoate, $C_{38}H_{62}O_2Si_2$, C 80 $S_B$ 82 I.

[(S)-(+)-2-Octyl]-4-[4-(5,5,7,7-tetramethyl-5,7-disilaoctyl)phenylethyl]benzoate, $C_{33}H_{50}O_2Si_2$, isotropic at 20° C.

[4-Propyl-1-bicyclo[2.2.2.]octyl]-4-(7,7,9,9,-tetramethyl-7,9-disiladecyloxy)benzoate, $C_{30}H_{52}O_3Si_2$, C 63N 66 I.

4'-Cyano-4-biphenylyl]-4-(5,5,7,7-tetramethyl-5,7-disilaoctyloxy)benzoate, $C_{30}H_{37}NO_2Si_2$, C 72 $S_A$ 180 I.

4'-Propyl-4-bicyclohexylyl]-4-(7,7,9,9-tetramethyl-7,9-disiladecyloxy)benzoate, $C_{34}H_{60}O_3Si_2$, C ($S_F$ 32 $S_B$) 49 $S_B$ 74 $S_A$ 106N 111 I.

Preparation of silanes:

Preparation of 2,4,4-trimethyl-2,4-disilapentane, $(CH_3)_3SiCH_2$—$Si(CH_3)_2H$:

A Grignard reaction was started with 2 ml of chloromethyltrimethylsilane (available from Janssen, 4057 Brüggen) and 15 g (0.62 mol) of magnesium in tetrahydrofuran with iodoethane at 60° C. and, after it had started, the remaining amount of a total of 73.6 g (0.6 mol) of the silane dissolved in 150 ml of THF was added dropwise at 60°–70° C. over a period of 3 hours. This solution after cooling and decantation was added dropwise at 15° C. to a stirred solution containing 51 g (0.54 mol) of chlorodimethylsilane in 150 ml of THF, and then the mixture was stirred at room temperature for 2 hours, the precipitate was removed by filtration and the filtrate was poured onto ice. After acidification with hydrochloric acid and extraction by shaking with methyl tert-butyl ether, the resulting organic phase was worked up in a known manner. Fractionation of the concentrated residue yielded 69.3 g (87.6% of theory) of the desired silane at 112°–116° C.

Preparation of 2,5,5,7,7-pentamethyl-2,5,7-trisilaoctane $(CH_3)_3SiCH_2Si(CH_3)_2—CH_2—CH_2Si(CH_3)_2H$:

In a procedure analogous to the above paragraph, a Grignard solution was prepared from 68 g (0.55 mol) of chloromethyltrimethylsilane in 150 ml of THF and was then added dropwise at 10° C. to a solution containing chlorodimethylvinylsilane, (available from ABCR GmbH, 7500 Karlsruhe) (2 hours). The mixture was then warmed to room temperature and finally kept at 35° C. for 1 hour, during which a voluminous precipitate formed. Hydrolysis, extraction by shaking with methyl tertbutyl ether, phase separation and working up resulted in 106 g of crude product which on fractionation yielded 68 g (corresponding to 72% of theory) of 3,3,5-trimethyl-3,5-disila-1-hexene $(C_8H_{20}Si_2)$ at 149°–151° C.

About 50 g (0.53 mol) of chlorodimethylsilane were added dropwise to 68 g (0.39 mol) of this silane and stirred at 60° C. in the presence of platinum catalyst (100 ppm Pt). The temperature of the mixture rose, owing to the heat of reaction, to 85° C. and was kept at this temperature. Continuation of the reaction at 80° C. for 30 minutes was followed by fractionation. About 77.4 g (74.3% of theory) of 2-chloro-2,5,5,7,7-pentamethyl-2,5,7-trisilaoctane were obtained at 108°–112° C. under 16 hPa. $C_{10}H_{27}ClSi_3$.

About 77.4 g (0.29 mol) of the chlorosilane described above were added dropwise to a suspension containing 3.2 g (0.084 mol) of $LiAlH_4$ in 150 ml of absolute ether while stirring at 10°–30° C. over a period of 3 hours. Continuation of the reaction at room temperature for 4 hours was followed by cautious decomposition of the excess alanate with water, and the mixture was made basic with 10 ml of 5N NaOH and the phases were separated. After working up the ether phase, the distilled residue yielded 62.5 g (92.9% of theory) of 2,5,5,7,7-pentamethyl-2,5,7-trisilaoctane at 82°–83° C. under 134 Pa. $C_{10}H_{28}Si_3$.

The following silanes were prepared by analogous procedures:

2,5,5-Trimethyl-2,5-disilahexane, boiling point 129° C., $C_7H_{20}Si_2$.

2,5,5,8,8-Pentamethyl-2,5,8-trisilanonane, boiling point 78°–80° C. under 5 hPa, $C_{11}H_{30}Si_3$.

6-(4-Methyl-3-cyclohexenyl1)-4,4,6-trimethyl-2,4-disilaheptane, boiling point 130°–131° C. under 8 hPa, $C_{16}H_{34}Si_2$.

2,6,6-Trimethyl-2,6-disilaheptane, boiling point 50° C. under 16 hPa, $C_8H_{22}Si_2$.

2,2,4,6,6-Pentamethyl-2,4,6-trisilaheptane, boiling point 66° C. under 16 hPa, $C_9H_{26}Si_3$.

2,4,4,7,7-Pentamethyl-3-oxa-2,4,7-trisilaoctane, boiling point 60° C. under 8 hPa, $C_9H_{26}OSi_3$.

2,4-Dimethyl-4-phenyl-2,4-disilapentane, boiling point 101°–102° C. under 16 hPa, $C_{11}H_{20}Si_2$.

2,5,8,8-Tetramethyl-5-(trimethylsilylmethyl)-2,5,8-trisilaoctane, boiling point 96°–97° C. under 5 hPa, $C_{13}H_{36}Si_4$, $[(CH_3)_3SiCH_2]_2Si(CH_3)—CH_2CH_2—Si(CH_3)_2H$.

Example 2

Comparison Example (a)

About [4-(4-Propyl-1-cyclohexenyl-1)phenyl]-4-[4-(pentamethyldisilozanyl)butyl]benzoate $(C_{31}H_{46}O_3Si_2)$, which has the following phase behavior: C (50 $S_c$) 65 $S_G$ 88 $S_c$ 93 I, can be prepared by reacting [4-(4-propyl-1-cyclohexenyl-1)phenyl]-4-(3-butenyl)benzoate (compare Example 1, examples of unsaturated esters) with pentamethyldisiloxane using a platinum catalyst in the manner described in Example 1.

Compared with the completely analogous compound of this invention, which is described in Example 1 (d), in which only the oxygen between the two Si atoms is replaced by a $CH_2$ group, in this case the melting point is 20° C. higher and the phase range of the smectic C phase on heating is only 5° C. compared with 41° C. for the compound of this invention.

Comparison Example (b)

The compound [4'-cyano-4-biphenylyl]-4-(4-trimethylsilylbutyl)benzoate, which is not in accordance with this invention, was prepared analogous to Example 1 (d), and has the following phase behavior: C 104 $S_A$ 191 I.

This compound which is not in accordance with the invention, has only the trimethylsilyl radical. It was compared with [4'-cyano-4-biphenylyl]-4-(5,5,7,7-tetramethyl-5,7-disilaoctyl)benzoate of Example 1 (d), and otherwise is identical.

The melting point for the compound of this invention is 32° C. lower, and has a 21° wider phase range.

Example 3

Process Example (c)

About 33.3 g (0.2 mol) of 4-(3-butenyl)-1-chlorobenzene prepared in accordance with Example 1 (b) were silylated with 2,4,4-trimethyl-2,4-disilapentane (compare Example 1 (d) with Pt as catalyst to give 1-chloro-4-(5,5,7,7-tetramethyl-5,7disilaoctyl)benzene. The boiling point was 115° C. under 0.05 hPa, and the yield was 70.8% of theory.

About 4-(5,5,7,7-Tetramethyl-5,7-disilaoctyl)benzoic acid was prepared in the same manner as described in Example 1 (b) from the above Si-alkyl-chlorobenzene by a Grignard compound by reaction with $CO_2$ (yield 51% of theory) with a melting point of 112°–113° C. $C_{17}H_{30}Si_2O_2$.

Reaction of this acid with thionyl chloride in toluene as solvent resulted in 4-(5,5,7,7-tetramethyl-5,7-disilaoctyl)benzoyl chloride in 89.6% yield (boiling point 165° C. under 0.05 hPa) $(C_{17}H_{29}ClOSi_2)$.

About 3.9 g (0.02 mol) of 4-cyano-4'-hydroxybiphenyl and 2 g of triethylamine were dissolved in 90 ml of toluene at 90° C., 6.8 g (0.02 mol) of the above acid chloride were added, and the mixture was stirred at 100° C. for 90 minutes. It was then cooled, filtered and concentrated. The crude product was recrystallized from ethanol/methanol (1:1) (yield 70%). The substance $(C_{30}H_{37}NO_2Si_2)$ showed the following phase behavior: C 72 $S_A$ 180 I.

Example 4

Process Example (b)

A Grignard reaction was started with 13.4 g (0.55 mol) of magnesium and 80.5 g (0.5 mol) of 4-chlorobenzyl chloride dissolved in 450 ml of diethyl ether, beginning with an initial amount of 10 ml, and was then completed in 3 hours at 10°–15° C. The decanted solution was added dropwise at room temperature to a solution containing 125 g (0.5 mol) of 3-chloropropyl 4-toluenesulfate (obtainable by simple esterification of 3-chloropropanol; boiling point 156° C. under 0.02 hPa) and subsequently heated at 60° C. for 2 hours. It was then cooled, hydrolyzed and worked up. Fractionation of the organic portion resulted in 55 g of 1-chloro-4-(4-chlorobutyl)benzene at 166°–168° C. under 16 hPa. A second Grignard solution was prepared from 40.6 g (0.2 mol) of this product and 5.3 g (0.22 mol) of magnesium and was then reacted at 30°–50° C. with 3.6 g (0.2 mol) of Si-chloropenta-Si-methyl-Si, Si′-methanediylbissilane (which can be prepared, for example, by the method of Kumada et al., J. Org. Chem. 23,292 (1958); boiling point 41° C. under 16 hPa). This resulted in a 65% yield of 1-chloro-4-(5,5,7,7-tetramethyl-5,7disilaoctyl)benzene (boiling point 115° C. under 0.05 hPa).

The product is identical to the first intermediate from Example 3 and can be reacted in the same manner to give 4-(5,5,7,7-tetramethyl-5,7-disilaoctyl)-benzoic acid, and the latter can be reacted further to give compounds of this invention.

Example 5

Preparation of [4-[4-(5,5,7,7-tetramethyl-5,7-disilaoctyl)phenyl]ethylphenyl]-3-fluoro-4-[(S)-2-methylbutoxy]-benzoate 4-($C_2H_5CH(CH_3$)—$CH_2O$)-3—F—$C_6H_3$-COO—$C_6H_4$—$(CH_2)_2$—$C_6H_4$—$(CH_2)_4$—$Si(CH_3)_2$—$CH_2$—$Si(CH_3)_3$ by process (a):

About 4.5 g (0.02 mol) of 3-fluoro-4-[(S)-2-methylbutoxy]benzoic acid (which can be prepared, for example, as described in EP-A 255 962 ), 5.0 g ( 0.02 mol) of 4-[4-(3-butenyl)phenylethyl]phenol, 4.1 g (0.02 mol) of dicyclohexylcarbodiimide and 0.1 g of 4-dimethylaminopyridine were mixed in 40 ml of ether at room temperature. The mixture was first heated to reflux for 4 hours and then stirred at room temperature for 14 hours, and the resulting urea was filtered off. Washing was carried out first with 2N hydrochloric acid and then with $NaHCO_3$ solution, and the ether phase was worked up. Column chromatography on $Al_2O_3$ with methyl tert-butyl ether/petroleum ether (1:2) as mobile phase resulted in 4.9 g of [4-[4-(3-butenyl)phenyl]ethylphenyl]-3-fluoro-4-[(S)-2-methylbutoxy]benzoate (yield 53.9%) which showed the following phase behavior: C 77 N* 86 I.

Hydrosilylation of this ester with 2,4,4-trimethyl-2,4disilapentane with Pt catalysis as in Example 1 (d) resulted in the desired compound ($C_{36}H_{51}FO_3Si_2$; 56.1% yield) which then showed the following phases compared with the unsilylated compound: G -44 $S_c$* 38 I.

Example 6

Preparation of 4-(6-ethyl-2-pyridylethenyl)phenyl 4-(5,5,-7,7-tetramethyl-5,7-disilaoctyl)benzoate by process (c).

The pyridylethenylphenol required was prepared by heating 72.6 g (0.6 mol) of 2-methyl-5-ethylpyridine and 73.2 g (0.6 mol) of 4-hydroxybenzaldehyde in 125 ml of acetic anhydride 155° C. for 20 hours, then cooled and poured into a mixture 300 ml of methanol and 60 ml of concentrated hydrochloric acid. After boiling under reflux (62° C.) for 3 hours, it was then cooled. About 120 ml of 25% ammonia and 10 g of sodium acetate were added and the precipitated product was removed by filtration. Recrystallization from 1.25 l of ethanol resulted in 42.8 g of product (31.6% of theory) which melted at 227° C. $C_{15}H_{15}NO$.

About 5.8 g (0.017 mol) of 4-(5,5,7,7-tetramethyl-5,7-disilaoctyl)benzoyl (preparation described in example 3) were added dropwise at 20° C. to 3.4 g (0.015 mol) of 5-ethyl-2-[2-(4-hydroxyphenyl)ethenyl]- pyridine and 2.1 ml of triethylamine in 350 ml of toluene/tetrahydrofuran (1:2.5). It was stirred for 3 hours, then heated to reflux for 4 hours. After cooling, the precipitate was removed by filtration and then concentrated. The residue was recrystallized from ethanol and then twice more from methanol. About 4.7 g (59.5% of theory) of the desired compound were obtained with the following phase behavior: C 64 $S_f$ 102N 105 I.

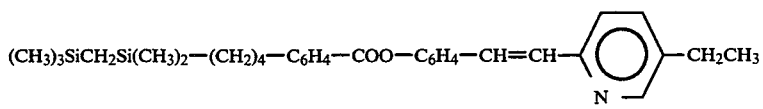

This compound could not be obtained by silylation of the analogous 4-(3-butenyl)benzoic ester since the pyridyl nitrogen blocked the Pt catalyst.

Example 7

Preparation of [4-(5-propyl-1,3-dioxan-2-yl)phenyl]-4-(5,5,7,7,-tetramethyl-5,7-disilaoctyl)benzoate by process (a).

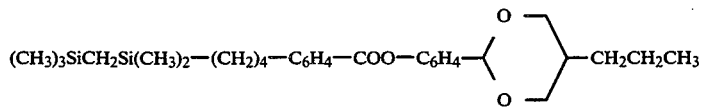

Diethyl-2-propylmalonate, which can be purchased, was reduced in a known manner with lithium aluminum hydride at 25°–30° C. to form 3-hydroxymethylpentanol. 4-Hydroxybenzaldehyde, which can be purchased, was esterified with 4-(3-butenyl) benzoyl chloride (preparation described in Example 1) at 20°–30° C. using triethylamine as auxiliary base. The 4-formylphenyl 4-(3-butenyl)benzoate prepared in this manner ($C_{18}H_{16}O_3$) melted at 49° C.

About 14 g (0.05 mol) of this formyl ester and 5.9 g (0.05 mol) of the above mentioned diol were heated to reflux with 0.1 ml of sulfuric acid in 150 ml of toluene, and the water formed in the reaction was removed by azeotropic distillation. Cooling, neutralization, washing and concentration resulted in a crude product which, after recrystallization from n-heptane, showed the following phases: C 100N 182 I. The yield was 54.7% of theory.

About 4.57 g (0.012 mol) of the above product were mixed with 2.02 g (0.015 mol) of 2,2,4-trimethyl-2,4-disilapentane in 10 ml of methylene chloride containing 0.4 ml of 0.5% dicyclopentadienylplatinum dichloride solution at room temperature. The mixture heated up to 30° C. within 60 minutes and was then stirred for 12 hours. The concentrated residue was chromatographed on silica gel. The yield was 61.3% of theory, $C_{30}H_{46}O_4Si_2$. The compound showed the following phase behavior: c (56N) 71 I.

Example 8

Preparation of [4-(5-hexyl-2-pyrimidinyl)phenyl]-4-(6,68-tetramethyl-6,8-disilanonyl)benzoate by process (a):

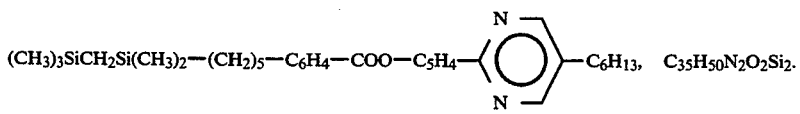

4-(4-pentenyl)benzoyl chloride was esterified with 5-hexyl-2-(4-hydroxyphenyl)pyrimidine with triethylamine as auxiliary base. The resulting (62.5% yield) 1-(5-hexyl-2-pyrimidinyl)phenyl]-4-(4-pentenyl)benzoate ($C_{28}H_{34}NO_2O_2$) showed the following phase behavior: C 52 N 139 I.

About 3 g (0.007 mol) of this ester were hydrosilylated with 1.1 g (0. 0075 mol) of 2,4,4-trimethyl-2,4-disilapentane (preparation described in Example 1) using 5 ml of a 0.5% solution of dicyclopentadienyl-platinum dichloride in 12 ml of dichloromethane at 60° C. in the manner described in Example 1. Chromatography of the crude product on silica gel with petroleum ether/dichloromethane (1:2) resulted in the pure desired product which has the following phase behavior: C 41 $S_c$ 44 $S_A$, N 48N 67 I.

Preparation of 2-[4-(5,5,7,7-tetramethyl-5,7-disilaoctyloxy)phenyl]-5-hexylpyrimidine by process (c).

Reaction of the pyridine derivative described above (Na salt) with the toluenesulfonate of 5,5,7,7-tetramethyl-5,7-disilaoctanol resulted in the desired compound: $C_{26}H_{44}N_2OSi_2$. It showed the following phase behavior: C 25N 48 I.

Example 9

Preparation of [(S)-(−)-1-cyano-2-methylpropyl)-4'-(10,10,12,12-tetramethyl-10,12-disilatridecyloxy)biphenyl-4-carboxylate by process (c).

A solution containing 4.5 g (0.022 mol) of N,N'-dicyclohexylcarbodiimide in 30 ml of dichloromethane was added dropwise to a solution containing 9.6 g (0.02 mol) of 4'-(10,10,12,12-tetramethyl-10,12-disilatridecyloxy(-biphenyl-4-carboxylic acid and 4.1 g ( 0.02 mol) of 4-N-pyrrolidinopyridine (=N—PPY) in 110 ml of dichloromethane, and the mixture was stirred at room temperature for 18 hours. The resulting urea was then filtered off and the crude product was purified by chromatography on silica gel with dichloromethane/heptane (4:1). This ester (90% yield) was then cleaved by hydrogenation by the method of L. K. M. Chan et al. (Mol. Cryst. Liq. Cryst. 1989, 172, 125). The free acid produced in this manner was converted with oxalyl chloride/ammonia into the corresponding amide. Reaction with thionyl chloride in DMF provided the desired compound. Phase behaviour: C 45 I.

What is claimed is:

1. A compound of the general formula

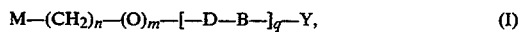

in which M represents a radical of the general formula

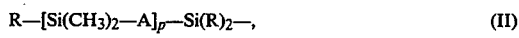

in which A is a bridging element selected from the group consisting of a methylene 1,2-ethylene and 1,3-propylene group; R is a straight-chain $C_1$-to $C_4$-alkyl group or a phenyl radical; and p is 1 or 2; n is an integer of from 3 to 12; m is 0 or 1; or M-$(CH_2)_n$—$(O)_m$ taken together is a 10-(4-methylcyclohex-3-enyl-1,5,5,8,8-tetramethyl-5,8-disilaundecyl) group or a 5,5,8,10,10-pentamethyl-8-trimethylsilylmethyl-5,8,10-trisilaundecyl group; D is a radical selected from the group consisting of 1,4-phenylene radicals, 1,4-cyclohexylidene radicals, 1,4-cyclohexenylidene radicals, 2,5-pyridinediyl radicals; 2,5-pyrimidinediyl radicals, 2,5-dioxanediyl radicals and 1,4-bicyclo[2.2.2]octanediyl radicals; B is a linking group selected from the group consisting of a chemical bond, —COO—, —OOC—, —$CH_2$—$CH_2$— and a —CH=CH— group; q is 2 or 3; Y is a hydrogen atom or a straight-chain or branched chain $C_1$- to $C_{10}$-alkyl group or $C_1$- to $C_{10}$-alkoxy group or a phenyl or cyclohexyl radical which is provided with a hydrogen atom or substituted, in which 1 or 2 ring substituents may be $C_1$- to $C_4$-alkyl, $C_1$- to $C_5$-alkoxy radicals, fluorine, or chlorine atoms or cyano radicals, or a cholesteryl radical.

2. A process for preparing the compound of claim 1 which comprises reacting a compound of the general formula MH with a compound of the general formula

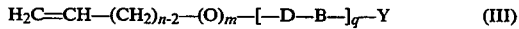

in the presence of at least one metal of the platinum group and/or its compounds, where M, A, R, n, m, D, B, q, Y and p are the same as in claim 1, with the proviso that the hydrogen atom in MH is bonded to a silicon atom.

3. A process for preparing the compound of claim 1 which comprises reacting halogenosilane compounds of the general formula M—Hal in which Hal represents a chlorine, bromine or iodine atom with a compound of the general formula

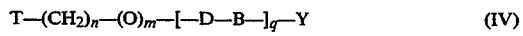

in which T is an alkali metal atom or Mg—Hal, where Hal is the same as above, with the elimination of a metal halide T—Hal, where M, A, R, n, m, D, B, q, Y and p are the same as in claim 1, with the proviso that when B and/or Y react with alkali metals or magnesium or compounds of the general formula IV, B and/or Y are added only after M—Hal has reacted with a compound of the formula IV.

4. A process for preparing the compound of claim 1 which comprises reacting a compound of the general formula $$M-(CH_2)_n-(O)_m-[-D-B-]_{r-1}-D-G \quad (V)$$

with a compound of the general formula $$Q-[-D-B-]_s-Y \quad (VI)$$

where r and s each are integers of from 0 to 3 whose total is q, G and Q each represent one of the radicals —OH, —OLi, —ONa, —OK, —O—$C_1$— to —O—$C_4$-alkyl, —COOH, —COBr, —COCl, —$NH_2$, —O—tos or —MgHal and M, A, R, n, m, D, B, q, Y and p are the same as in claim 1, and Hal forms linking group B and elimination of compounds W which represent water, $C_1$-to $C_4$-alkanol, HHal, $MgHal_2$, LiHal, NaHal, KHal, Li—O—tos, Na—O—tos or K—O—tos.

5. A liquid crystalline compound comprising at least one compound of claim 1, which displays nematic, smectic and/or cholesteric phases.

6. An information storage system containing the compound of claim 1.

7. An electrographic process containing the compound of claim 1.

8. A signal generator containing the compound of claim 1.

* * * * *